United States Patent [19]

Duquette et al.

[11] Patent Number: 4,684,729

[45] Date of Patent: Aug. 4, 1987

[54] POLYETHYLENE POLYPIPERAZINE COMPOSITIONS

[75] Inventors: Lawrence G. Duquette, Maynard; Philip E. Garrou, Holliston, both of Mass.

[73] Assignee: The Dow Chemical Company, Midland, Mich.

[21] Appl. No.: 861,018

[22] Filed: May 7, 1986

Related U.S. Application Data

[63] Continuation of Ser. No. 514,080, Jul. 15, 1983, abandoned.

[51] Int. Cl.$^4$ .................. C07D 403/12; C07D 403/13; C08G 73/06
[52] U.S. Cl. .................................... 544/357; 528/422; 528/423
[58] Field of Search ................ 344/357; 528/422, 423

[56] References Cited

U.S. PATENT DOCUMENTS

| | | | |
|---|---|---|---|
| 3,285,920 | 11/1966 | Muhlbauer et al. | 544/402 X |
| 3,297,700 | 1/1967 | Muhlbauer et al. | 544/402 X |
| 3,364,218 | 1/1968 | Brader | 544/357 |
| 3,761,522 | 9/1973 | Schneider et al. | 260/239 E |
| 4,216,307 | 8/1980 | Yaasa et al. | 564/463 |
| 4,374,243 | 2/1983 | Yaasa et al. | 564/463 |

*Primary Examiner*—Nicholas S. Rizzo
*Assistant Examiner*—William A. Teoli, Jr.

[57] ABSTRACT

The invention is the process which comprises contacting a reaction mixture comprising between about 1 and 100 percent by weight of a polyethylene-substituted piperazine, a piperazine or mixtures thereof, wherein such compounds contain a primary or secondary nitrogen wherein one of the carbons adjacent to the nitrogen has a hydrogen atom bonded to the carbon atom, and between about 1 and 99 percent of a solvent, with a catalytic amount of palladium on a support, at a temperature of between about 150° C. and 300° C., under condition such that the product so prepared contains polyethylene polypiperazines.

22 Claims, No Drawings

POLYETHYLENE POLYPIPERAZINE COMPOSITIONS

This is a continuation of application Ser. No. 514,080, filed July 15, 1983, now abandoned.

BACKGROUND OF THE INVENTION

The invention relates to novel polyethylene polypiperazines and a process for preparing them.

By-products of processes for the preparation of ethyleneamines include mixtures of polyethyleneamines, polyethyleneamine-substituted piperazines and piperazines. Disposal of the latter two by-products creates a substantial problem for manufacturers of ethyleneamines.

What is needed is a method for disposing of such by-products. What is most desirable is to convert these by-products to useful products.

SUMMARY OF THE INVENTION

In one aspect, the invention is a process for converting such piperazine by-products to useful polymers which comprises contacting a reaction mixture comprising (a) between about 1 and 100 percent by weight of a polyethyleneamine, a polyethyleneamine-substituted piperazine, a piperazine or mixtures thereof, wherein such compounds contain a primary or secondary nitrogen wherein one of the carbon atoms adjacent to the primary or secondary nitrogen has a hydrogen atom bonded thereto, and (b) between about 0 and 99 percent of a solvent, with a catalytic amount of palladium on a support under conditions such that polyethylene polypiperazines, polyethyleneamines or mixtures thereof are prepared.

Another aspect of this invention is the novel compounds which are polyethylene polypiperazines.

The products of this process are useful as flocculants and de-emulsifiers. Such products are useful in the preparation of polyamines.

DETAILED DESCRIPTION OF THE INVENTION

The starting reactants in this invention are polyethyleneamines, polyethyleneamine-substituted piperazines, piperazines or mixtures thereof wherein such compounds contain a primary or secondary nitrogen which is bonded to a carbon atom which has a hydrogen atom bonded thereto. Such starting reactants include polyethyleneamines which correspond to the formula

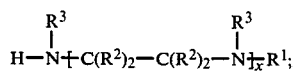

polyethyleneamine-substituted piperazines corresponding to the formula

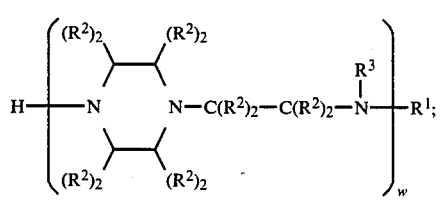

and piperazines corresponding to the formula

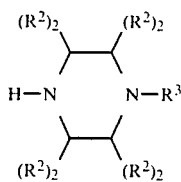

wherein $R^1$ is separately in each occurrence hydrogen or corresponds to the formula

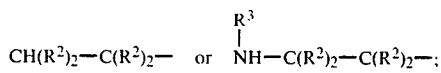

$R^2$ is separately in each occurrence hydrogen or $C_{1-20}$ hydrocarbyl;

$R^3$ is separately in each occurrence hydrogen or $C_{1-20}$ hydrocarbyl;

w is separately in each occurrence an integer of from 1 to 20 inclusive; and x is separately in each occurrence an integer of from 1 to 20 inclusive.

In the above formulas $R^2$ is preferably hydrogen or $C_{1-10}$ alkyl, more preferably hydrogen or $C_{1-3}$ alkyl, and most preferably hydrogen. $R^3$ is preferably hydrogen or $C_{1-10}$ alkyl, more preferably hydrogen or $C_{1-3}$ alkyl, and most preferably hydrogen. Preferably u is an integer of from 4 to 20 inclusive.

Hydrocarbyl means herein an organic radical containing carbon and hydrogen atoms. The term hydrocarbyl includes the following organic radicals: alkyl, alkenyl, alkynyl, cycloalkyl, cycloalkenyl, aryl, aliphatic and cycloaliphatic, aralkyl and alkaryl. Aliphatic refers herein to straight- and branched- and saturated and unsaturated hydrocarbon chain, that is, alkyl, alkenyl or alkynyl. Cycloaliphatic refers herein to saturated and unsaturated cyclic hydrocarbons, that is, cycloalkenyl and cycloalkyl. The term aryl refers herein to biaryl, biphenylyl, phenyl, naphthyl, phenanthranyl, anthranyl and two aryl groups bridged by an alkylene group. Alkaryl refers herein to an alkyl-, alkenyl- or alkynyl-substituted aryl substituent wherein aryl is as defined hereinbefore. Aralkyl means herein an alkyl, alkenyl or alkynyl group substituted with an aryl group, wherein aryl is as defined hereinbefore. Alkyl includes straight- and branched-chain methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl groups. Alkenyl further refers to the above-named groups in which there are two or more double bonds, for example, butadiene, pentadiene, hexadiene, heptadiene and the like. Alkynyl further refers to the above-named groups wherein there are two or more triple bonds.

Cycloalkyl refers to alkyl groups containing one, two, three or more cyclic rings. Cycloalkenyl refers to mono-, di- and polycyclic groups containing one or more double bonds. Cycloalkenyl also refers to cycloalkenyl groups wherein two or more double bonds are present, for example, cyclobutadienyl, cyclopentadienyl and cyclohexadienyl groups.

Generally, the process of this invention comprises contacting piperazines, polyethyleneamines, polyethyleneamine-substituted piperazines or mixtures thereof wherein such compounds contain a primary or secondary nitrogen which is bonded to a carbon atom to which is bonded a hydrogen atom with a catalytic amount of palladium on a support.

When contacted with the palladium catalyst, the reactants can either be in neat form or dissolved in a solvent. Depending upon the composition, the reactant mixture can be either in solid or liquid form. Where the reactant mixture is liquid under reaction conditions no solvent is necessary. Where the reactant mixture is solid under reaction conditions a solvent is necessary. The amount of solvent which is used depends upon the composition of the reactant mixture and the particular solvent chosen. Desirable amounts of solvent are those amounts which dissolve the reactant mixture.

Generally the reaction mixture comprises between about 1 and 100 percent by weight of the reactants, and between about 0 and 99 percent by weight of a solvent. Preferably the reaction mixture comprises between about 10 and 100 percent by weight of the reactants and between about 0 and 90 percent by weight of a suitable solvent. More preferably, the reactant mixture comprises between about 25 and 100 percent by weight of reactants and 0 and 75 percent by weight of a suitable solvent.

A suitable solvent is any solvent (1) in which the reactants are soluble, (2) which is inert to the reactants under reaction conditions, and (3) which is stable under reaction conditions. Among desirable solvents are aromatic hydrocarbons, for example, benzene, toluene, ethylbenzene, xylene, etc.; ethers; cyclic ethers; pyridines; aliphatic hydrocarbons, for example, heptane, octane, nonane, and the like; and tertiary amines. Preferable solvents are aromatic hydrocarbons and pyridines.

The catalyst is palladium on a support. Any form of palladium which deposits metal on a support is useful in this invention. Generally, any support which has structural integrity and will interact with palladium to form the necessary electronic forces so as to hold the palladium on the support is suitable. Any support known in the art is suitable. Desirable supports include carbon, aluminas, zeolitic alumino-silicates, silicalites, silica gel, activated clays, silicon carbide, etc. Preferable supports include carbon or alpha-alumina. A more preferable support is carbon.

A catalytic amount of catalyst is that amount which catalyzes the reaction described herein. Generally, the amount of palladium required to catalyze the reaction depends upon the load capacity of palladium, the palladium crystallite size, the available surface area of the palladium to the reactants, the percent dispersion of the palladium, the contact time between the reactants and the catalyst, the concentration of the reactants in any solvent, and the particular product mix desired.

Preferably, a mole ratio of reactants to palladium of between about 25:1 and 1000:1, more preferably mole ratios are between about 50:1 and 100:1.

More important is the surface area of the palladium available to the reactants. A surface area of between about 4 m²/g and 50 m²/g is desirable. A preferable surface area is between about 25 and 50 m² /g.

Related to available surface area is the crystallite size of the palladium. The smallest the crystallite size is, the more surface area there is available to catalyze the reaction. A crystallite size of between about 10 and 300 Å is desirable, a preferable crystallite size is between 50 and 150 Å. Also related to available surface area of palladium is percent dispersion. A percent dispersion of palladium is between about 10 and 75, preferable percent dispersions are between 40 and 75.

Desirable load capacities of palladium on the support are between about 0.1 and 100 percent, preferably between about 5 and 10 percent.

Any temperature at which the reaction proceeds is suitable. The reaction temperature is preferably between about 150° C. and 300° C., more preferably between about 180° C. and 240° C.

The reaction generally requires a contact time of greater than 1 hour, preferably greater than 12 hours, and more preferably greater than 24 hours. Longer contact times result in a higher conversion of reactants to products.

The products prepared by the process of this invention generally comprise a mixture of polyethyleneamines and polyethylene polypiperazines. The polyethyleneamines comprise a mixture of polymeric materials, which have as a repeating unit ethyleneamine, of various sizes and molecular weights. The polyethylene polypiperazines comprise polymeric compositions which contain ethylene and piperazinylene units and terminate in alkylamine, alkyl or hydrogen compounds. Further, some of these polyethylene polypiperazines contain ethyleneamine internal units.

The product prepared generally contains water-soluble and water-insoluble components. The water-soluble components include the polyethyleneamines and the polyethylene polypiperazines having less than four piperazine units per molecule. The water-insoluble component comprises polyethylene polypiperazines having four or more piperazine units per molecule.

The ethyleneamines prepared by the process described herein correspond to the formula

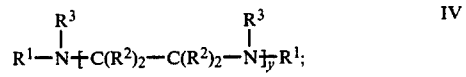

the novel polyethylene polypiperazines correspond to the formula

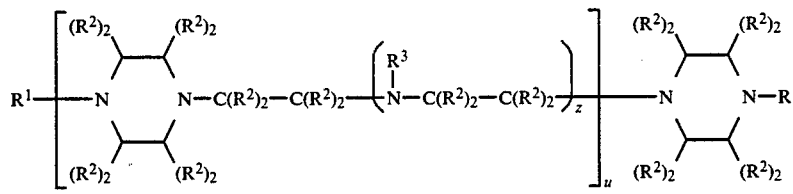

wherein $R^1$, $R^2$ and $R^3$ are as defined above; z is separately in each occurrence an integer of between about 0 and 10; and u is an integer of from 1 to 20.

In one preferred embodiment, the novel polyethylene polypiperazines correspond to the formula

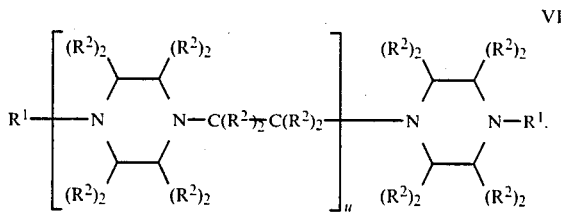

VI

In this embodiment, the internal units are ethylene and piperazine units. When u is 3 or more, the compounds are water-insoluble.

The relative ratio of the polyethyleneamines to the polyethylene polypiperazines in the final product is dependent on the reaction conditions. The reaction generally goes in stages and the product mix depends upon the stage to which the reaction is allowed to proceed. Intermediates in the formation of polyethylene polypiperazines are polyethyleneamine piperazines in which there are some nitrogens which are not part of piperazine rings. Theoretically, if the reaction is run to completion the product would be predominantly polyethylene polypiperazines.

The product of this process can comprise between about 0 and 100 percent by weight of ethyleneamines and between 0 and 100 percent by weight of the polyethylene polypiperazines.

The process conditions can be altered to get certain products or product mixtures. The amount of polyethylene polypiperazines in the product is increased by the use of higher temperatures, longer contact times, higher concentrations of reactants in the solvent, by the use of more catalyst and by using a catalyst with more surface area, for example, by using a more dispersed catalyst or a catalyst with smaller crystallite size.

The polyethylene polypiperazines are generally insoluble in any solvent or reaction mixture at about 20° C. to 25° C. Thus, these compounds are easily recovered.

The process described herein can be practiced by either batch or continuous reaction schemes. In continuous reaction schemes the product mixture can be recycled through the reactor until the desired product composition is achieved.

SPECIFIC EMBODIMENTS

The following examples are included for illustrative purposes only and are not intended to limit the scope of the invention or the claims. All parts and percentages are by weight unless otherwise specified.

EXAMPLE 1

Reaction of Piperazine

To the reactor is added 10 g (0.116 mole) of piperazine in 75 ml of toluene (13 percent piperazine) and 5 g of 10 percent palladium on carbon powder. The reaction is sealed and stirred at 180° C. for 12 hours. After the reactor has cooled, there is vented into 10 ml of $H_2O$ 46 psi of a vapor. The vapor smells like $NH_3$ and a gas chromatograph peak overlaps an injection of ethylamine.

The catalyst is filtered from the toluene reaction solution and washed with toluene and methanol. The filtrate is evaporated at reduced pressure to a yellow gum (9.6 g) and this gum in turn is washed with hot water (approximately 100 ml). After cooling, a light yellow precipitate is filtered off and allowed to air dry giving a gummy solid which on washing with ether gives 1.5 g of a dry white solid. No gas chromatograph of the solid is obtainable but a $C^{13}$ nuclear magnetic resonance spectrum shows the material to be a polyalkylene polypiperazine. A size exclusion chromatograph provides a molecular weight determination of approximately 630, which would approximate to the following structure

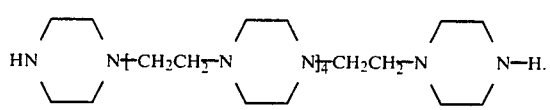

Evaporation of the aqueous filtrate yields 7.5 g of a yellow waxy gum. A gas chromatograph of this gum shows the presence of a wide spectrum of polyalkylene polypiperazines. A $C^{13}$ nuclear magnetic resonance gives evidence that the polyalkylene polypiperazines are capped with ethyl groups. Both the gas chromatograph and $C^{13}$ nuclear magnetic resonance show low molecular weight species and this is verified by size exclusion chromatography.

The mass balance is calculated as follows:

| Conversion: | 100% |
|---|---|
| Selectivity: | |
| gaseous product | approximately 4% |
| R.T. $H_2O$ insoluble | 21% |
| R.T. $H_2O$ soluble | 75% |

EXAMPLE 2

Reaction of Aminoethylpiperazine

To the reactor is added 100 g (0.077 mole) of aminoethyl piperazine in 75 ml of toluene (13 percent aminoethyl piperazine) and 5 g of 10 percent palladium on carbon powder. The reactor is sealed and stirred at 180° C. for 12 hours.

After the reactor has cooled, there is vented into 10 ml of water 53 psi of a vapor. The vapor smells like $NH_3$ and a gas chromatograph peak overlaps an injection of ethylamine.

The catalyst is filtered from the toluene reaction solution and washed with toluene and methanol. The filtrate is evaporated at reduced pressure to a yellow gum (8.9 g). The $C^{13}$ nuclear magnetic resonance and gas chromatograph are similar to those obtained from piperazine. The reaction gives a conversion of 79.5 percent.

EXAMPLE 3

Reaction of a Mixture of Ethyleneamines

Still bottoms from an ethyleneamine process which comprise 1 percent triethylenetetramine isomers (TETA), 20 percent triethylenepentamine isomers (TEPA), 53 percent pentaethylenehexamine isomers (PEHA), and 26 percent hexaethyleneheptane isomers (HEHA) (10 g, approximately 0.033 mole), are added to the reactor in 75 ml of toluene (13 percent of the ethyleneamines) and 5 g of 10 percent Pd/C powder. The reactor is sealed and stirred at 180° C. for 12 hours.

After the reactor has cooled, there is vented into 10 ml of water approximately 30 psi of a vapor. The vapor smells like NH₃ and a gas chromatograph peak overlaps an injection of ethylamine.

The catalyst is filtered from the toluene reaction solution and washed with toluene and methanol. The filtrate is evaporated at reduced pressure to a yellow gum (9.7 g). The $C^{13}$ nuclear magnetic resonance and gas chromatograph are similar to those obtained from piperazine. The reaction gives a conversion of 79.5 percent.

EXAMPLE 4

Reaction of Polyethyleneamines

The polyethylenimine mixture has a $M_w$ of 550–600, and contains the following percentages of amine linkages: 25 percent —CH₂CH₂—NH₂, 50 percent —CH₂CH₂—NH— and 25 percent

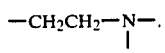

To the reactor is added 3 g (approximately 0.005 mole) of the ethyleneamine mixture in 75 ml of toluene (4.4 percent ethyleneamines) and 5 g of 10 percent palladium on carbon powder. The reactor is sealed and stirred at 180° C. for 12 hours.

After the reactor has cooled, no pressure buildup is observed.

The catalyst is filtered from the toluene reaction solution and washed with toluene and methanol. The filtrate is evaporated at reduced pressure to a yellow gum (2.5 g). The $C^{13}$ nuclear magnetic resonance and gas chromatograph are similar to that obtained from piperazine (Example 1). The reaction gives a conversion of 79.5 percent.

What is claimed is:

1. A process for the preparation of polyethylene polypiperazines comprising contacting piperazines, ethyleneamine-substituted piperazines, or mixtures thereof, wherein such compounds contain a primary or secondary nitrogen and wherein one of the carbon atoms adjacent to the primary or secondary nitrogen has a hydrogen atom bonded thereto, with a catalytic amount of palladium on a support, under conditions whereby the polyethylene polypiperazines are prepared.

2. The process of claim 1 wherein the piperazine and ethyleneamine-substituted piperazine are dissolved in a suitable solvent.

3. The process of claim 2 wherein the piperazines correspond to the formula

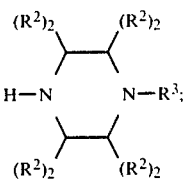

the polyethyleneamine-substituted piperazines correspond to the formula

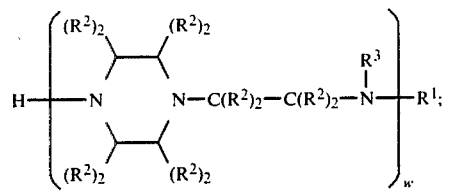

and the polyethylene polypiperazines correspond to the formula

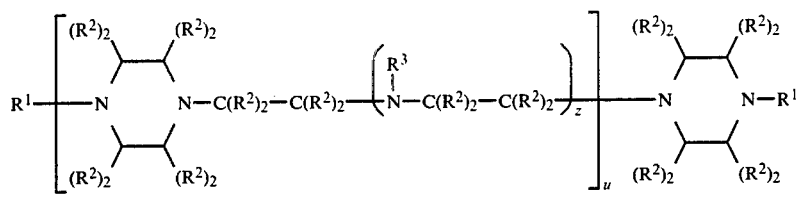

wherein

R¹ is separately in each occurrence hydrogen or corresponds to the formula

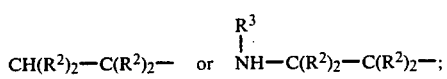

R² is separately in each occurrence hydrogen or C₁₋₂₀ hydrocarbyl;

R³ is separately in each occurrence hydrogen or C₁₋₂₀ hydrocarbyl;

w is separately in each occurrence an integer of from 1 to 20 inclusive;

z is separately in each occurrence an integer of between about 0 to 10; and u is an integer of from 1 to 20, with the proviso that one of the carbon atoms adjacent to the primary or secondary amines on the polyethyleneamine-substituted piperazine and the piperazines have a hydrogen atom bonded to the carbon atom.

4. The process of claim 3 wherein R² is hydrogen or C₁₋₁₀ alkyl.

5. The process of claim 3 wherein R² is hydrogen or C₁₋₃ alkyl.

6. The process of claim 3 wherein R² is hydrogen.

7. The process of claim 3 wherein R³ is hydrogen or C₁₋₁₀ alkyl.

8. The process of claim 3 wherein R³ is hydrogen or C₁₋₃ alkyl.

9. The process of claim 3 wherein R³ is hydrogen.

10. The process of claim 3 wherein u is an integer of from 4 to 20 inclusive.

11. The process of claim 3 wherein z is an integer of from 0 to 3 inclusive.

12. The process of claim 3 wherein z is the integer 0.

13. The process of claim 2 wherein the temperature is between about 150° C. and 300° C.

14. The process of claim 2 wherein the temperature is between about 180° C. and 240° C.

15. The process of claim 2 wherein the support is carbon or alpha-alumina.

16. The process of claim 2 wherein the solvent is an aromatic hydrocarbon, an ether or a cyclic ether.

17. A process for the preparation of polyethylene polypiperazines comprising contacting a reaction mixture containing between 1 and 100 percent by weight of piperazines, ethyleneamine-substituted piperazines or mixtures thereof, and between 1 and 99 percent by weight of a solvent, wherein the piperazine reactants contain a primary or a secondary nitrogen wherein one of the carbon atoms adjacent to the nitrogen has a hydrogen bonded to the carbon atom, with a catalytic amount of palladium on a support at a temperature of between about 150° C. and 300° C.

18. The process of claim 17 wherein the temperature is between about 180° C. and 240° C.

19. The process of claim 18 wherein the support is carbon or alpha-alumina.

20. The process of claim 18 wherein the reaction mixture comprises between about 25 and 100 percent by weight of polyethyleneamine-substituted piperazine, piperazine, or mixtures thereof, and between 0 and 75 percent by weight of a solvent.

21. The process of claim 18 wherein the percent dispersion of palladium is between about 40 and 80.

22. The process of claim 18 wherein the contact time is greater than about 24 hours.

* * * * *